United States Patent
Weiler et al.

(10) Patent No.: US 11,552,995 B2
(45) Date of Patent: Jan. 10, 2023

(54) AUTOMATIC NETWORK PROVISIONING OF A MEDICAL DEVICE

(71) Applicant: CareFusion 303, Inc., San Diego, CA (US)

(72) Inventors: Aron Weiler, San Diego, CA (US); Jeff Gaetano, Wittmann, AZ (US); Brian Sullivan, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 323 days.

(21) Appl. No.: 16/805,559

(22) Filed: Feb. 28, 2020

(65) Prior Publication Data

US 2020/0287937 A1     Sep. 10, 2020

Related U.S. Application Data

(60) Provisional application No. 62/814,765, filed on Mar. 6, 2019.

(51) Int. Cl.
*H04L 29/06*     (2006.01)
*H04L 9/40*      (2022.01)
(Continued)

(52) U.S. Cl.
CPC .............. *H04L 63/18* (2013.01); *G16H 40/40* (2018.01); *G16H 40/67* (2018.01); *H04L 63/0823* (2013.01)

(58) Field of Classification Search
CPC ..... H04L 63/0823; H04L 63/18; G16H 40/40; G16H 40/67
See application file for complete search history.

(56) References Cited

U.S. PATENT DOCUMENTS 9,161,377 B2    10/2015 Cloutier
9,880,528 B2 *   1/2018 Mastrototaro ......... G05B 15/02
(Continued)

OTHER PUBLICATIONS

Serdar Cabuk et al., Towards Automated Provisioning of Secure Virtualized Networks, Oct. 2007, ACM, pp. 235-245. (Year: 2007).*
(Continued)

*Primary Examiner* — Luu T Pham
*Assistant Examiner* — Fahimeh Mohammadi
(74) *Attorney, Agent, or Firm* — Morgan, Lewis & Bockius LLP

(57) ABSTRACT

One or more medical devices are configured to connect to a predetermined temporary provisioning network of a healthcare organization, the temporary provisioning network being different than a healthcare network of the healthcare organization. After the devices are received by the healthcare organization, and powered up for the first time, device identifiers corresponding to the medical devices are received at a server remote from the healthcare organization, from the temporary provisioning network, together with an indication that the medical devices are requesting access to a management server within a healthcare network of the healthcare organization. On determining that the medical devices are predetermined to receive access to the management server, a provisioning service configures, through the temporary provisioning network, the medical devices to access and communicate with the management server, and informs the management server that the medical devices have been configured to access and communicate with the management server.

23 Claims, 4 Drawing Sheets

(51) Int. Cl.
*G16H 40/67* (2018.01)
*G16H 40/40* (2018.01)

(56) References Cited

U.S. PATENT DOCUMENTS

| | | | | |
|---|---|---|---|---|
| 10,291,477 | B1* | 5/2019 | Askar | H04W 4/50 |
| 10,419,908 | B1* | 9/2019 | Hutz | H04L 61/6022 |
| 10,771,261 | B1* | 9/2020 | Lazar | H04L 9/3268 |
| 11,050,570 | B1* | 6/2021 | Totah | H04L 9/3215 |
| 2009/0031410 | A1* | 1/2009 | Schneider | H04L 63/0823 726/10 |
| 2009/0217364 | A1* | 8/2009 | Salmela | H04W 12/068 726/6 |
| 2010/0138523 | A1* | 6/2010 | Urness | G16H 40/67 709/222 |
| 2010/0138524 | A1 | 6/2010 | Sobie | |
| 2014/0281503 | A1* | 9/2014 | Mills | H04L 9/3268 713/157 |
| 2014/0373118 | A1* | 12/2014 | Doi | H04L 9/3268 726/6 |
| 2015/0215974 | A1* | 7/2015 | Cloutier | H04W 84/105 455/405 |
| 2015/0370973 | A1* | 12/2015 | Jones | G16H 20/17 705/2 |
| 2017/0093587 | A1* | 3/2017 | Glisson | H04L 63/062 |
| 2018/0137307 | A1* | 5/2018 | Srinivasan | G06F 21/72 |
| 2019/0223248 | A1* | 7/2019 | Chandran | H04L 12/2803 |
| 2020/0106837 | A1* | 4/2020 | Brickell | H04W 12/00 |
| 2021/0306157 | A1* | 9/2021 | Wattiau | H04L 9/3247 |

OTHER PUBLICATIONS

Kuan Zhang et al., Security and Privacy for Mobile Healthcare Networks: From a Quality of Protection Perspactive, Aug. 27, 2015, IEEE, vol. 22, Issue: 4, pp. 104-112. (Year: 2015).*

Marcos A. Simplicio Jr. et., Privacy-preserving method for temporarily linking/revoking pseudonym certificates in VANETs, Sep. 6, 2018, IEEE, Oages: 1322-1329. (Year: 2018).*

Jieun Song et al., SHOES : Secure Healthcare Oriented Environement Service Model, Aug. 15, 2008, IEEE, pp. 89-93. (Year: 2008).*

Written Opinion of the International Preliminary Examining Authority for Application No. PCT/US2020/021258, dated Mar. 23, 2021, 5 pages.

International Preliminary Report on Patentability for the International Preliminary Examining Authority for Application No. PCT/US2020/021258, dated Jun. 22, 2021, 19 pages.

International Search Report and Written Opinion for Application No. PCT/US2020/021258, dated Jun. 2, 2020, 16 pages.

Mehta, T. et al, "Auto-Provisioning of Biomedical Devices on a Converged IP Network", Biomedical Instrumentation & Technology 463 IT World, Nov. 30, 2009 (Nov. 30, 2009), pp. 463-467, XP055688305, Retrieved from the Internet: URL:https://www.aami-bit.org/doi/pdf/10.2345/0899-8205-43.6.463 [retrieved on Apr. 22, 2020] p. 465 bullet point 1-p. 466 bullet point 7.

* cited by examiner

AUTOMATIC NETWORK PROVISIONING OF A MEDICAL DEVICE

CROSS REFERENCE TO RELATED APPLICATIONS

This application claims the benefit of U.S. Provisional Application Ser. No. 62/814,765, entitled "AUTOMATIC NETWORK PROVISIONING OF A MEDICAL DEVICE," filed on Mar. 6, 2019, the entirety of which is incorporated herein by reference.

TECHNICAL FIELD

This application relates generally to automatically provisioning medical devices such as infusion devices to healthcare networks of healthcare organizations.

BACKGROUND

Medical devices such as infusion devices purchased for use in healthcare organizations typically require manual configuration to connect to the healthcare network of the healthcare organization. Typically, an operator configures and installs necessary security certificates and updates for compliant use on the healthcare network. This process is often difficult and time consuming to set up each medical device.

With the ever-growing need for new advanced medical devices, the need to automatically connect additional medical devices to healthcare networks has increased. Efficient provisioning methods to connect multiple medical devices to healthcare networks are desired.

SUMMARY

Configuring dozens of medical devices for use on a healthcare network is arduous and time consuming. A major concern for healthcare organization includes reducing the set up time for healthcare devices while maintaining strict security protocols. Traditionally, each medical device is manually configured by an operator to access the healthcare network.

Accordingly, there is a need for methods and systems that can automatically configure a medical device to an appropriate healthcare network without manual intervention. Disclosed implementations are able to securely and efficiently provision multiple devices for use on a healthcare network.

The disclosed subject matter relates to a method for automatically provisioning multiple medical devices on a network. In accordance with some implementations, the method includes configuring one or more medical devices to connect to a predetermined temporary provisioning network of a healthcare organization. The temporary provisioning network is different from the healthcare network of the healthcare organization. After the devices are received by the healthcare organization, and powered up for the first time, device identifiers corresponding to the medical devices are received at a server remote from the healthcare organization, from the temporary provisioning network, together with an indication that the medical devices are requesting access to a management server within a healthcare network of the healthcare organization. On determining that the medical devices are predetermined to receive access to the management server, a provisioning service configures, through the temporary provisioning network, the medical devices to access and communicate with the management server, and informs the management server that the medical devices have been configured to access and communicate with the management server.

The disclosed subject matter also relates to a machine-readable medium embodying instructions that, when executed by a machine, allow the machine to perform a method for automatic network provisioning described herein.

The disclosed subject matter also relates to a system for automatic network provisioning. The system includes one or more processors and a memory including instructions that, when executed by the one or more processors, cause the one or more processors to perform the steps of the method described herein.

The subject technology provides a system for automatically provisioning a medical device, including one or more processors and a memory. The memory includes instructions that, when executed by the one or more processors, cause the one or more processors to configure one or more medical devices to connect to a predetermined temporary provisioning network of a healthcare organization responsive to the one or more medical devices being powered on for a first time, the temporary provisioning network being different than the healthcare network of the healthcare organization, receive, from the temporary provisioning network, one or more device identifiers corresponding to the one or more medical devices and an indication that the one or more medical devices requests access to the healthcare network, determine, based on receiving the one or more device identifiers, that the received one or more device identifiers correspond to respective medical devices predetermined to receive access to a management server within the healthcare network, in accordance with a determination that the one or more medical devices are predetermined to receive access to the healthcare network and the management server, configure, through the temporary provisioning network, the medical devices to access and communicate with the management server, and confirm that the one or more medical devices have been configured to access and communicate with the management server. Other aspects include corresponding methods, apparatus, and computer program products for implementation of the corresponding system and its features.

According to other aspects, the subject technology provides a medical device that includes a non-volatile data storage unit that stores (a) predetermined provisioning network connection information and (b) identification information uniquely identifying the medical device, one or more processors, and a memory. The memory includes instructions that, when executed by the one or more processors, causes the one or more processors to, upon activation of the medical device, determine that the activation is an initial activation at a healthcare facility based at least in part on an activation indicator stored by the medical device, establish, responsive to determining the activation is the initial activation, a first network connection with a provisioning network based at least in part on the predetermined provisioning network connection information, transmit, via the first network connection, the identification information uniquely identifying the medical device, receive, via the first network connection, facility network connection information for accessing and communicating with a management server associated with the healthcare facility, and establish, after receiving the facility network connection information and using a second network different than the provisioning network, a second network connection with the management server based at least in part on the facility network connection information.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Medical devices are preconfigured to efficiently configure themselves when powered on for the first time. The medical devices may be preconfigured during manufacturing or by a supplier to include information allowing automatic provisioning of the device, including installation of software to connect to a private healthcare network. For example, when an order is placed by a hospital for new medical devices, the new medical devices may be preconfigured (e.g., during manufacturing) to connect (e.g., wirelessly) to a special provisioning network operated by the hospital. This temporary provisioning network may be publicly accessible and separated from a main network, so that the main network remains protected from unauthorized access. The provisioning network is then used by the devices on power up to configure themselves by installing the required software and security information for accessing the hospital's main network.

Any required security certificates and/or software updates are effected by the healthcare network through the temporary provisioning network. Once the medical device is compliant with the healthcare network's requirements, the medical device is granted access to the healthcare network and the temporary provisioning network connection may be terminated. The temporary provisioning network may act as a safeguard to protect security breaches while configuring medical devices to access the healthcare network.

Figure 1:
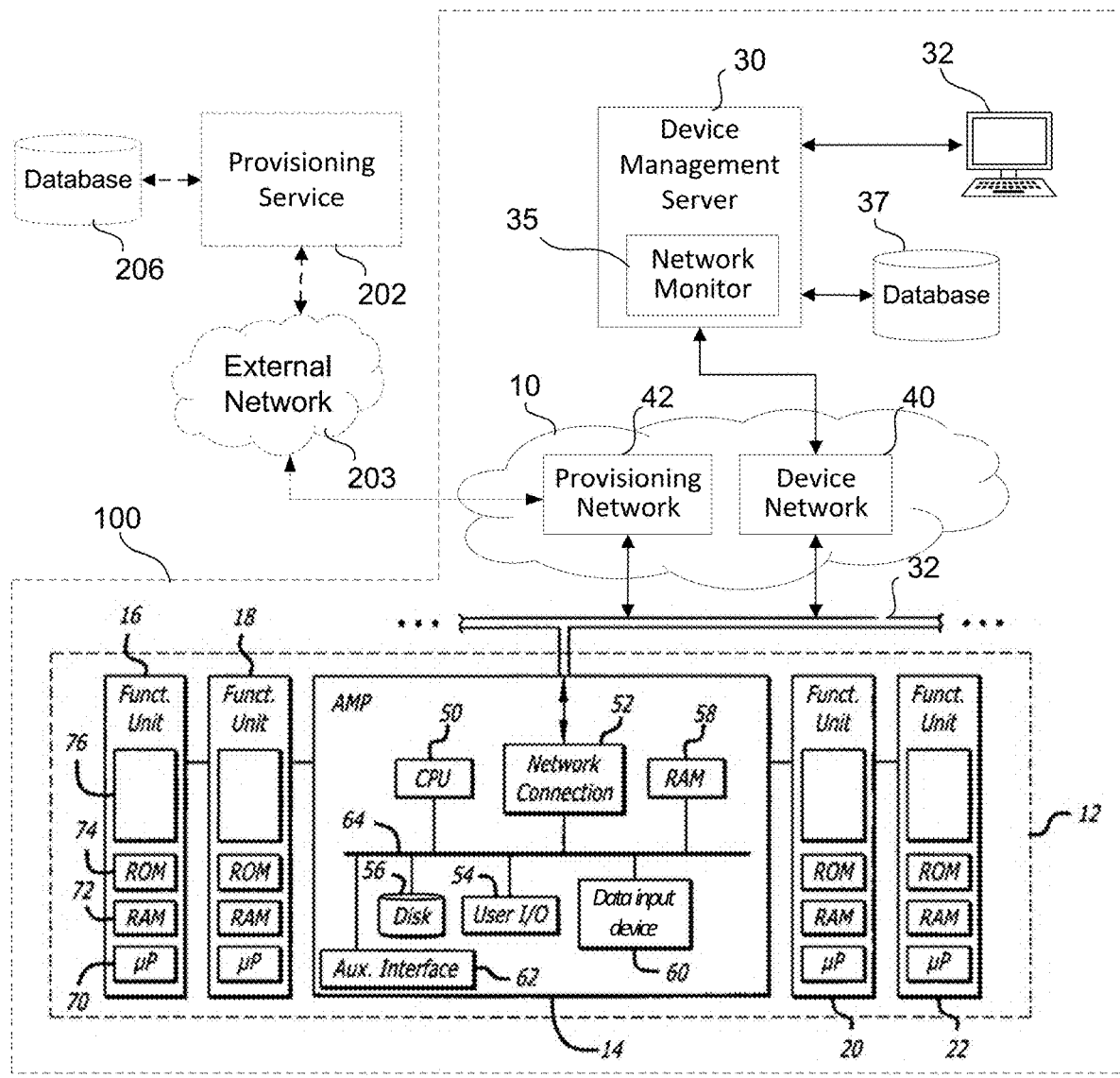
FIG. 1 depicts an example of an institutional patient care system of a healthcare organization, according to aspects of the subject technology.

FIG. 1 depicts an example of an institutional patient care system 100 of a healthcare organization, according to aspects of the subject technology. In FIG. 1, a patient care device 12 is connected to a hospital network 10. The term patient care device (or "PCD") may be used interchangeably with the term patient care unit (or "PCU"), either which may include various medical devices such as an infusion pump, a vital signs monitor, a medicant dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to a healthcare network 10 by a transmission channel 32. Transmission channel 32 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations, and a provisioning network 42 by which the devices may connect upon start up to load certain parameters required for operation within the institutional patient care system 100 environment. According to some implementations, the devices and supporting services of network 10 or a portion thereof may be cloud-based with, for example, the servers and services (e.g., databases, APIs, etc.) located remote from the hospital and/or distributed across multiple remote locations or regions.

Additionally, institutional patient care system 100 may incorporate a separate device management server 30, the function of which will be described in more detail below. Moreover, although the device management server 30 is shown as a separate server, the functions and programming of the device management server 30 may be incorporated into another computer, such as, for example, a hospital information system server or cloud-based server, if such is desired by engineers designing the institution's information system. Institutional patient care system 100 may further include one or multiple device terminals 32 for connecting and communicating with device management server 30. Device terminals 32 may include personal computers, personal data assistances, mobile devices such as laptops, tablet computers, augmented reality devices, or smartphones, configured with software for communications with device management server 30 via network 10.

Patient care device 12 comprises a system for providing patient care, such as that described in U.S. Pat. No. 5,713,856 to Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices associated with control module 14 for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 1, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. In some implementations, a functional module may include hardware components similar to those of control unit 14 including, but not limited to, a CPU 50 connected to a memory, RAM 58, one or more interface devices such as user interface device 54, a coded data input device 60, a network connection 52, and an auxiliary interface 62 for communicating with additional modules or devices. It should be noted that while four functional modules are shown in FIG. 1, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

According to various implementations, while each functional module may be capable of independent operation (e.g., as described with respect to control unit 14 and its hardware components), interface unit 14 is configured to monitor and control overall operation of device 12. For example, as will be described in more detail below, interface unit 14 may provide programming instructions to the functional modules 16, 18, 20, 22 and monitor the status of each module.

Patient care device 12 may be capable of operating in several different modes, or personalities, with each personality defined by a configuration database. A particular configuration database may be selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

Figure 2:
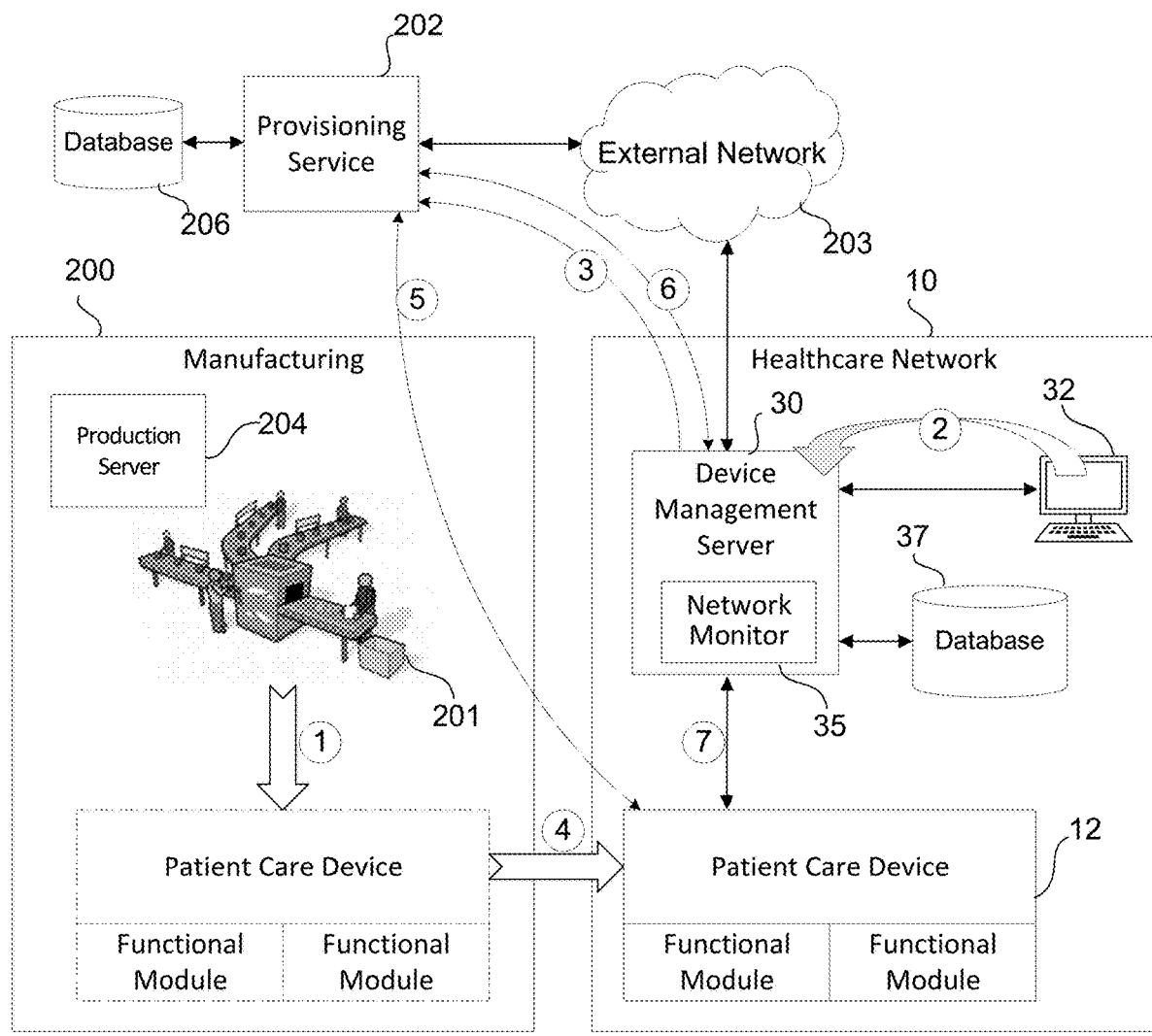
FIG. 2 depicts an example of information flow between various elements of an institutional patient care system and a provisioning service in accordance with aspects of the subject technology.

FIG. 2 depicts an example of information flow between various elements of institutional patient care system 100 and a provisioning service 202 in accordance with aspects of the subject technology. As shown, device management server 30 is in communication with one or multiple various patient related devices 12, such as an infusion pump, a point of care unit, a syringe pump, a vital signs monitor, automated medication dispensing machine, or other medical device. Each of these patient related devices provide therapy to a patient or monitor the patient's vital signs or condition, and provide information about the status of the patient and the patient's therapy to the server. A network monitoring application program 35 provides an interface with the server, and thus all of the assets in communication with the server. Using the network application program 35, users such as a pharmacist, nurse, physician and biomedical technician may view the information provided to the server by the various patient assets, may adjust the therapy being provided to the patient, or may monitor the operation of the patient assets. Such a system is particularly useful in that it provides a pathway for the software configurations of the patient assets to be altered or updated by a qualified biomedical technician.

A client-server environment incorporating aspects of the subject technology may include a central server (e.g., device management server 30) that is accessible by at least one client via a computer network. In more complex systems, the central server may be accessible by at least one local server via a computer network, such as, for example, an Ethernet, wireless network, or the Internet which may in turn be accessed by a client. A variety of computer network transport protocols including, but not limited to TCP/IP, can be utilized for communicating between the central server, any local servers, and client devices configured with a communications capability compatible with the communication protocol used on the network.

The device management server 30 generally includes or uses a central database 37, such as a SQL server application program, or the like, executing thereon. The device management server 30 may ensure that the local servers are running the most recent version of a knowledge base, and also may store all patient data and perform various administrative functions including adding and deleting local servers and users to the system. The device management server 30 may also provide authorization before a local server or client medical device can be utilized by a user. As stated previously, in the example integrated systems, patient data may be stored on device management server 30, thereby providing a central repository of patient data. However, it is understood that patient data can be stored on a local server or on local storage media, or on another hospital or institutional server or information system, where it may be accessed through the various elements of the system, that is, by local servers or clients, as needed.

Local servers (and the services they provide) may be implemented in connection with device management server 30. Each local server may serve, for example, multiple users in a particular geographical location. Examples of such a local server may include servers located in hospital wards, at nurse stations or at off-site or remote locations operating either as primary or back-up information collection, routing, analysis and/or storage systems. Each local server may include a server application, one or more knowledge bases, and a local database. Each local server may also include an inference system capable of interacting with sets of rules or practice criteria for ensuring that proper medical and medication delivery and prescribing practices are followed. Each local server may also perform artificial intelligence processing for carrying out operations of the subject technology. When a user logs on to a local server via a client, the user may be authenticated via an identification and password. Once authenticated, a user is permitted access to the system and certain administrative privileges are assigned to the user. Additionally or in the alternative, the system may be programmed to operate such that various patient, care-giver and medication identification devices, such as bar coded labels, RF identification tags or devices, or other smart, passive or active identification devices may be used to identify users of the systems and allow access to the system for diagnosing and treating patients. Scanning of such devices may be performed at patient care device 12, for example, using data input device 60.

Each local server may also communicate with the device management server 30 to verify that the most up-to-date version of the knowledge base(s) and application(s) are running on the requesting local server. If not, the requesting local server downloads from device management server 30 the latest validated knowledge base(s) and/or application(s) before a user session is established. While in some implementations of the subject technology most of the computationally intensive work, such as data and artificial intelligence processing, is performed on a local server, allowing "thin" clients (that is, computing devices having minimal hardware) and optimizing system speed, the subject technology is also intended to include systems where data processing and rules processing is carried out on the clients, freeing the central system, or local server, from such tasks.

Each local client or medical device also includes a client application program that may include a graphical user interface (GUI), although such is not necessary on many medical devices, and a middle layer program that communicates with central or local servers. Program code for the client application program may execute entirely on the local client, or it may execute partly on the local client and partly on the central or local server.

Computer program code for carrying out operations of the subject technology may be written in an object oriented programming language such as, for example, JAVA®, Smalltalk, or C++. However, the computer program code for carrying out operations of the subject technology may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

All direct communications with medical devices operating on a network in accordance with the subject technology may be performed through device management server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication channels with them.

Prior to implementation within institutional patient care system 100, patient care devices 12 may be configured during their manufacturing with default network information for allowing the devices to connect a designated provisioning service for receiving specific configuration information for normal operation within institutional patient care system 100 including, for example, network information and/or security information for connecting to network 10 and to device management server 30.

When patient care devices 12 are received at a healthcare facility of the healthcare organization, an administrator may, via a terminal device 32, create records for the devices in database 37. In this regard, each record may include a unique identification (ID) of a respective device 12 (e.g., a serial number, media access control address, mobile device identifier, device name, and the like). The unique ID may be affixed to the device (e.g., as a printed label or RFID tag) or stored in an internal memory, and captured by a scanner device such as a bar code reader or RFID reader device. In some implementations, the unique ID may be transmitted using a wireless connection (e.g., BLUETOOTH). A respective record created for a device may map the unique ID to specific configuration information. As described further below, this configuration information and mapping is then provided to a provisioning service which will be accessed by the device on power up. In some implementations, the unique IDs of the device(s) may be electronically received by device management server 30, for example, via an external network 203 such as the Internet or other WAN. Device management server 30 may provide a user interface for acceptance and/or confirmation of the device(s) to receive the configuration information prior to the configuration information being provided to the provisioning service 202.

In accordance with various implementations, device management server 30 may be responsible for managing access of patient care devices 12 to network systems of the institutional patient care system 100, communications between the various devices over network 10, and routine management of patient care devices 12. In this regard, device management server 30 may provide, via terminal device(s) 32, a user interface for assignment of the one or more device identifiers to one or more security certificates. The security certificates, once installed on the patent care device(s) 12, enable the patient care device(s) to access and communicate with the device management server 30 and/or other devices within institutional patient care system 100.

In some implementations, the user interface provided by the management server, may facilitate an assignment of the device identifiers and security certificates to a respective facility within the healthcare organization. In this regard, configuring patient care device(s) 12 to access and communicate with device management server 30 comprises configuring patient care device(s) 12 to communicate via network 10 (or transmission channel 32) within the respective facility, with an encrypted security certificate specific to the respective facility.

FIG. 2 depicts information flow between various elements of an institutional patient care system 100 and a provisioning service 202 in accordance with various aspects of the subject technology. In example step 1, patient care device(s) 12 is manufactured 201 at a factory or other manufacturing environment 200. Patent care device(s) are manufactured with default network information allowing the device(s) to connect to a provisional service 202 when powered on for the first time. The default network information may be a global default or a default for an intended recipient of the patient care device(s).

According to various implementations, patient care device(s) 12 come preconfigured to seek a known SSID (service set identifier for a WiFi network) or other provisioning address (e.g., a IP or IP-subnet address) used at the medical facility (e.g., within institutional patient care system 100) responsive to being powered on. The manufacturer or supplier may inform all facilities in which the patent care device(s) will be operated to use this provisioning mechanism so the devices will recognize the provisioning mechanism out-of-the-box and be able to communicate with provisioning service 202 over an external network 203 (e.g., a WAN or Internet). In some implementations, a patient care device will be programmed to connect to the provisioning service using the provisioning address upon detecting a network connection, such as when connected to network 10, a WAN, or the Internet (e.g., via Ethernet or WiFi connection).

Provisioning service 202 may implement an interface for each medical facility to program its own internal healthcare network information. The patient care device(s) 12 are preconfigured to turn on and, if not previously provisioned with local network connection information and credentials, communicate with the provisioning service 202 through the predetermined provisioning network 42, download information for the respective internal healthcare network, and then reconfigure to connect through the healthcare network 40 and proceed to operate with the healthcare facility's internal servers (including, e.g., device management server 30) over the healthcare network 40. The pre-configuration may include setting an activation indicator (e.g., a flag) within non-volatile storage unit 56 of the patient care device(s) 12, which will then be checked on a power up by CPU 50 to determine whether the activation is an initial activation.

According to various implementations, provisioning service 202 may be implemented by a server external to healthcare network 10. For example, provisioning service may be implemented by software executing on a production server 204 within manufacturing environment 200. In some implementations, provisioning service 202 may be implemented as software executing on device management server 30. Provisioning service 202 may further implement or be connected to a provisioning database 206.

Prior to or in parallel with the manufacture of patient care device(s) 12, illustrated in step 2, an administrator enters specific configuration information (e.g., using a user interface provided to terminal device 32) for the device(s) to operate within institutional patient care system 100 including, for example, network information and/or security information for connecting to network 10 and to device management server 30. The network information may be assigned to a specific facility within the healthcare organization responsible for institutional patient care system 100. Also, the administrator may provide specific predetermined network connection information (e.g., Internet Protocol (IP) address(es), subnet addresses, SSID, network password or other connection credential, etc.) for provisioning network 42 and device network 40. Each patient care device 12 may be preconfigured with the network information for provisioning network 42 during the manufacturing process or by the supplier prior to being transferred to the healthcare organization. For example, a patent care device 12 may store the predetermined network connection information and identification information uniquely identifying the patent care device 12 in non-volatile storage unit 56.

Steps 3 and 4 are depicted as being ordered, but may occur in any particular order. In step 3, a unique ID associated with each device is further associated with the network information such as SSID(s) the patient care devices(s) may connect with during normal operations, security information, IP addresses, subnet addresses, DHCP server, DNS server, etc. This may be accomplished by entering the IDs at terminal device 32, scanning the devices themselves, or receiving the IDs from the manufacturer or supplier of the device in an electronic transfer to institutional patient care system 100 (e.g., received at device management server 30). In some implementations, device IDs may be assigned to each device when they are received by the healthcare organization (e.g., device ID to serial number assignment). The assigned device/unique IDs are then made available to provisioning service 202 (e.g., and provisioning database 206). For example, the data may be pushed to provisioning service 202, or provisioning service 202 may be integrated with device management server 30 such that, once entered, provisioning service 202 may look up the information on receiving an indication that the data is available.

In step 4, patient care device(s) 12 is received by the healthcare organization. Provisioning network 42 is specifically set up in advance for devices to connect through network 10 to provisioning service 202 (e.g., outside the healthcare organization via external network 203). This provisioning network may be publicly accessible, may be separated from a main hospital network, or may include a portion (e.g., a subnet) of the main hospital network. According to the depicted example, each device is configured at the factory (or by the supplier) to connect to provisioning network 42, and to connect to provisioning service 202. The connection (e.g., within network 10) may be by via Ethernet, WiFi, BLUETOOTH, or other network connection. In step 5, a respective device is powered on and automatically connects via the provisioning mechanism to provisioning service 202 using the predetermined provisioning mechanism. For example, upon activation of the device 12, the device may determine that the activation is an initial activation at a healthcare facility based at least in part on the activation indicator stored by the device. The device 12 may then, responsive to determining the activation is the initial activation, establish a network connection with provisioning network 42 based at least in part on the predetermined provisioning network connection information stored in non-volatile storage unit 56.

Once connected to the provisioning service 202, the patient care device 12 may transmit information including the unique ID (e.g., via provisioning network 42 and external network 203). The provisioning service 202 (e.g., operational on server 204) receives the information including the unique ID from the device and determines, based on receiving the information, that the device is predetermined to receive access to device management server 30 within institutional patient care system 100.

In accordance with this determination, provisioning service 202 configures, through the temporary provisioning network 42, the respective patient care device(s) 12 to access and communicate with device management server 30. In this regard, provisioning service 202 provides the device with the specific facility network connection information assigned to the unique ID. This connection information is received by device(s) 12 for use in accessing and communicating with management server 30. Each patient care device 12 may send its own respective device identifier to management server 30 through the temporary provisioning network 42. The management server 30 determines whether the patient care device(s) 12 and their device identifiers have been predetermined to receive access to the healthcare network 40. If the patient care device(s) 12 are to receive access, the management server 30 may send one or more security certificates for installation on the patient care device(s) 12. The management server 30 may also send optional device configuration files, firmware updates, software updates, and/or other security protocol for installation on the patient care device(s) 12. The management server 30 may then request confirmation of the configuration by patient care device(s) 12 from provisioning service 202.

After the device(s) are configured, provisioning service 202, illustrated by step 6 reports the configuration status to device management server 30. This report may be automatically initiated by provisioning service 202 or may be provided responsive to a request from device management server 30. Accordingly, device management server 30 may be configured to block (e.g., prevent) connections and/or communications for a device—even if assigned previously by server 30 to the network information via device network 40 until device management 30 receives confirmation from provisioning service 202 that configuration of the device was completed. Blocking connections or communications may include dynamically configuring network hardware (e.g., routers, access points, gateways, etc.) of the healthcare network 10 to alter the connectivity or packet handling associated with a device. The dynamic configuration may include transmitting a control signal to the network hardware or updating configuration information used by the network hardware (e.g., add identifier of the device to a blocked list, update network address routing table(s)).

The management server 30 may also receive an indication that the security certificates have been successfully installed on the requesting patient care device(s) 12. In some implementations, if the management server 30 does not receive an indication that the security certificates have been successfully installed, the management server 30 may decline granting access to the healthcare network. In some other implementations, the management server 30 may re-send the security certificates for installation.

Through the temporary provisioning network, the patient care device(s) 12 may receive access to communicate directly with the management server. In some implementations, patient care device(s) 12 also receive access to healthcare network 40. According to various implementations, once a patient care device 12 has been properly configured by provisioning service 202 and granted access to the healthcare network 40, the connection to temporary provisioning network 202 via provisioning network 42 is terminated. The patient care device(s) 12, as shown by step 7, may then connect to device management server 30 (e.g., for the first time) as fully configured devices (e.g., via network 10). In this regard, each device 12 may establish, using the healthcare network 40, an entirely new and different network connection with management server 30 based at least in part on the previously received facility network connection information.

In some implementations, during the forgoing provisioning process, a patient care device 12 may be configured to identify its location within patient care system 100, and transmit the location as part of the information transmitted to provisioning service 202. In this regard, the location may be detected using WiFi connection information within the system (e.g., mapping an SSID to a location), or device 12 may include location hardware (e.g., GPS) for identifying specific coordinates, which it may then send to provisioning service 202. On receiving this information, provisioning service 202 may select, based on the location, a specific server(s) within network 10 to which the patient care device 12 should connect with for normal operation, and send configuration information (including, e.g., the previously described connection information and/or security certificates, etc.) to patient care device 12 that is specific to the selected server(s).

Figure 3:
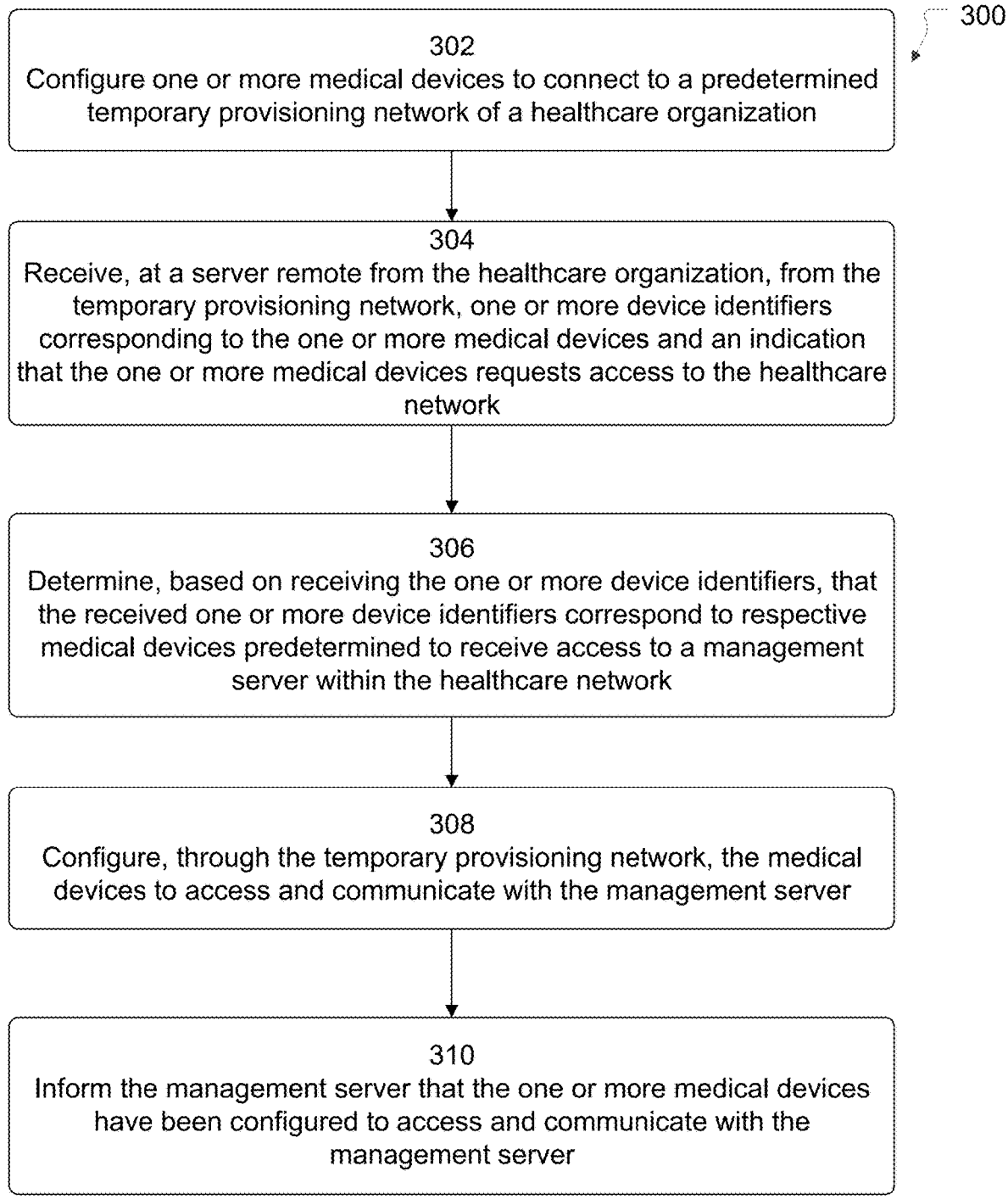
FIG. 3 depicts an example process for automatically provisioning medical devices to a healthcare network, according to aspects of the subject technology.

FIG. 3 depicts an example process for automatically provisioning medical devices to a healthcare network, according to aspects of the subject technology. For explanatory purposes, the various blocks of example process 300 are described herein with reference to FIGS. 1 and 2, and the components and/or processes described herein. The one or more of the blocks of process 300 may be implemented, for example, by one or more computing devices including, for example, production service 202 and/or production server 204 and/or other computing devices within factory or other manufacturing environment 200. In some implementations, one or more of the blocks may be implemented apart from other blocks, and by one or more different processors or devices. Further for explanatory purposes, the blocks of example process 300 are described as occurring in serial, or linearly. However, multiple blocks of example process 300 may occur in parallel. In addition, the blocks of example process 300 need not be performed in the order shown and/or one or more of the blocks of example process 300 need not be performed.

In the depicted example, one or more medical devices are configured to connect to a predetermined temporary provisioning network of a healthcare organization when the devices are powered on for the first time (302). According to various implementations, the temporary provisioning network is different than a healthcare network of the healthcare organization. The temporary provisioning network may be configured to broadcast a service set identifier (SSID) preconfigured to be known by the medical devices and the medical devices are configured to seek the SSID prior to being powered on for a first time at the healthcare organization. In some implementations, the provisioning may be triggered when a device is powered on, network connection is detected, and the facility connection information for a healthcare network is not specified or has expired. If the device determines that there is no facility connection information or that the facility connection information is no longer valid, the medical device may connect to the predetermined temporary provisioning network using the stored provisioning information.

For example, the one or more medical devices may be configured by a production server 204 distinct from the management server and outside of the healthcare organization. The medical devices may be configured during manufacturing process 201 or by a supplier of the devices or, in some implementations of the subject technology, by personnel or systems at the healthcare organization when the devices are received by the healthcare organization.

After the medical devices are transferred to the healthcare organization and received by the healthcare organization, one or more device identifiers corresponding to the one or more medical devices are received, from the temporary provisioning network 42, at a server remote from the healthcare organization, together with an indication that the one or more medical devices requests access to the healthcare network (304). This remote server may be, for example, a production server 204 or other server implementing provisioning service 202. According to various aspects, the healthcare organization creates temporary provisioning network 42 for the purpose of installing security certificates and/or updating software on the respective devices 12 for connecting the medical devices to a main device network 40. In some implementations, the device identifier is a serial number of the device, or some other unique identifier associated with the device. The device identifiers may be network addresses of the respective medical devices or any other device identifier capable of identifying a device.

Responsive to receiving the one or more device identifiers, the provisioning service 202 determines that the received one or more device identifiers correspond to respective medical devices predetermined to receive access to a management server within the healthcare network (306). In this regard, prior to this determination, production service 202 may receive, from device management server 30, one or more security certificates assigned to the one or more device identifiers.

In accordance with a determination that the one or more medical devices are predetermined to receive access to the management server, the provisioning service 202, facilitates the configuration, through the temporary provisioning network 42, the medical devices to access and communicate with the management server (308). This may include, for example, sending (e.g., electronically transmitting), to the one or more medical devices, through the temporary provisioning network, the one or more security certificates for installation on the medical devices to access the management server to configure the medical devices to access and communicate with the management server. This may include transmitting network credentials or configuration information such as DNS server, DHCP server, IP address, subnet address, SSIDs, access control lists (e.g., whitelist or blacklist), etc.

After the configuration is completed, the provisioning service 202 informs the management server 30 (e.g., by transmitting an electronic communication to server 30) that the one or more medical devices have been configured to access and communicate with the management server (310). In some implementations, a sever associated with provisioning service 202 (e.g., production server 204) confirms that the one or more medical devices have been configured to access and communicate with the management server.

In some implementations, a production server 202, distinct from the management server and outside of the healthcare organization, configures the one or more medical devices. For example, during manufacturing of the medical devices, a production server associated with the manufacturing process configures the medical device. In some implementations, the temporary provisioning network is configured to broadcast a service set identifier (SSID) preconfigured to be known by the medical devices and the medical devices are configured to seek the SSID prior to being powered on for a first time. Similarly, the medical devices may be preconfigured at a production server to seek the SSID of the temporary provisioning network. In some implementations, the temporary provisioning network is an Ethernet network and the healthcare network of the healthcare organization is a local area network (LAN).

In some implementations, the temporary provisioning network may be a personal area network such as a ZigBee or Bluetooth compatible network. In such instances, the medical device may seek a unique identifier associated with the compatible network. Once the medical device attaches to the personal area network, the medical device may continue provisioning as described. The personal area network may be managed by a hotspot or other access point device. The hotspot or access point may be carried onto the premises by a field service technician to facilitate deployment of the medical device. The hotspot or other access point device may serve as a conduit for communications between the medical device and the provisioning server. Once provisioning is complete, the hotspot or access point device may be disabled or removed from the premises. Using a personal area temporary provisioning network may be desirable to secure the provisioning of the medical device to a geographically limited area (e.g., within the coverage area of the PAN) and allowing the hotspot or access point device to communicate with the wider network (e.g., the Internet).

In some implementations, the management server is configured to receive, via a user interface provided by the management server, an assignment of the one or more device identifiers to the one or more security certificates, the management server being further configured to provide to a provisioning server outside the healthcare organization the one or more security certificates to the one or more medical devices on a power up of the medical devices, and to communicate with the one or more medical devices after being informed that the one or more medical devices have been configured to access and communicate with the management server.

In some implementations, the management server is configured to receive via the user interface provided by the management server, an assignment of the one or more device identifiers and the one or more security certificates to a respective facility of a plurality of facilities within the healthcare organization. Configuring the one or more medical devices to access and communicate with the management server includes configuring the one or more medical devices to communicate via a local network within the respective facility. The one or more security certificates are specific to the respective facility.

In some implementations, the method includes receiving, from the management server, one or more security certificates assigned to the one or more device identifiers, the one or more security certificates being received prior to determining that the received one or more device identifiers correspond to respective medical devices predetermined to receive access to the management server. The method further includes sending, to the one or more medical devices, through the temporary provisioning network, the one or more security certificates for installation on the medical devices to access the management server to configure the medical devices to access and communicate with the management server. In some implementations, the one or more medical devices includes an infusion device, a ventilator device, or an automated dispensing device.

In some implementations, configuring the medical devices to access and communicate with the management server includes downloading the one or more security certificates, installing the one or more security certificates, verifying that the security certificates have been installed successfully, and determining security standards of the healthcare network have been met.

In some implementations, configuring the medical devices includes receiving an indication that the medical devices have been successfully configured to access and communicate with the management server and terminating a network access of the medical devices to the predetermined temporary provisioning network.

If a determination does not indicate that the one or more medical devices are predetermined to receive access to the healthcare network and the management server, the server may not grant access to the healthcare network.

In some implementations, the features may be implemented to securely control the medical device. For example, the facility network configuration information or certificates may be associated with an expiration time. The expiration time may be set as part of the provisioning process. In some implementations, the device management server may transmit a message revoking or expiring the connection information globally or for specific devices. In some implementations, the medical device may be reset to a factory default configuration such as by activating a physical control (e.g., button) on the medical device. In such cases, the medical device, upon powering up, may determine that the facility network configuration is either expired or not specified. Upon such determination, the medical device may initiate connection to the temporary provisioning network to obtain a facility network configuration. This allows a facility to disable devices that may have been stolen from accessing the facility network. A user may access the device management server to specify the identifier of the lost device. This lost message may be transmitted to the provisioning server to prevent subsequent provisioning for the identifier. The features may be used to disable devices subject to a recall or requiring maintenance before further use. For example, the manufacturer of the medical device may provide a list of identifiers for devices subject to a recall.

The provisioning server may be configured to compare a received unique identifier for a medical device with the list of identifiers for stolen or recalled devices. If the request including an identifier included on the list, the provisioning server may transmit a message to the requesting device indicating the associated condition (e.g., device is disabled, device requires maintenance, device is recalled, etc.) that prevents provisioning. If the condition preventing provisioning is that the facility has not yet transmitted network information for the unique identifier, the provisioning server may, in response to receiving a request from the medical device, transmit a message indicating that no site specific information has been provided for provisioning a medical device associated with the identifier. The provisioning server may integrate with a transaction data store to identify a point of contact for a user responsible for the medical device. In such implementations, the provisioning server may cause transmission of a message to the user indicating the need for provisioning information for a particular medical device.

Many of the above-described example 300, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 4:
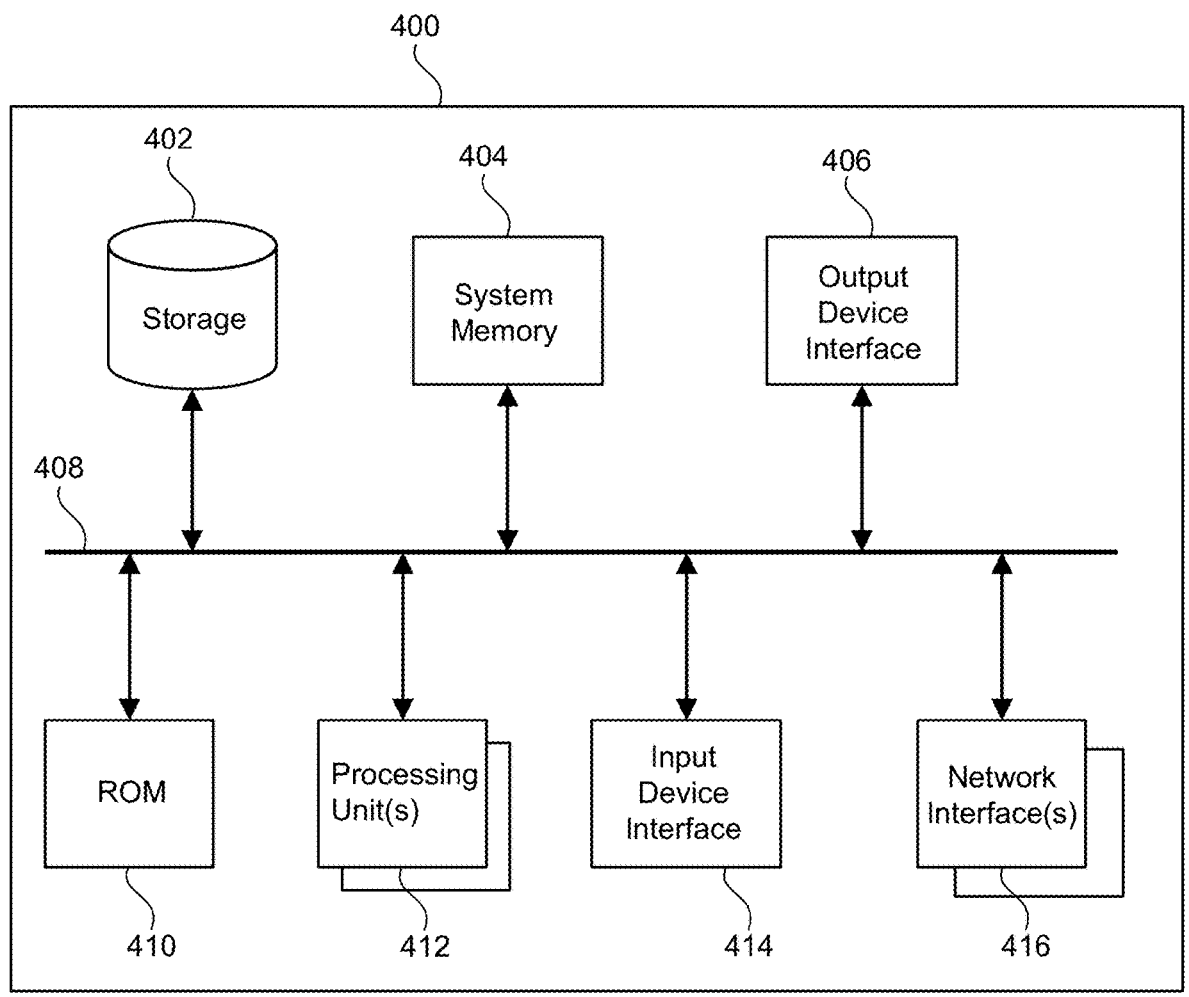
FIG. 4 is a conceptual diagram illustrating an example electronic system 400 for the automatic provisioning of medical devices, according to aspects of the subject technology.

FIG. 4 is a conceptual diagram illustrating an example electronic system 400 for the automatic provisioning of medical devices, according to aspects of the subject technology. Electronic system 400 may be a computing device for execution of software associated with one or more portions or steps of process 400, or components and processes provided by FIGS. 1-3, including but not limited to device management server 30, production server 204, computing hardware within patient care device 12, or terminal device 37. Electronic system 400 may be representative, in combination with the disclosure regarding FIGS. 1-3. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 400 may include various types of computer readable media and interfaces for various other types of computer readable media. In the depicted example, electronic system 400 includes a bus 408, processing unit(s) 412, a system memory 404, a read-only memory (ROM) 410, a permanent storage device 402, an input device interface 614, an output device interface 406, and one or more network interfaces 416. In some implementations, electronic system 400 may include or be integrated with other computing devices or circuitry for operation of the various components and processes previously described.

Bus 408 collectively represents all system, peripheral, and chipset buses that communicatively connect the numerous internal devices of electronic system 400. For instance, bus 408 communicatively connects processing unit(s) 412 with ROM 410, system memory 404, and permanent storage device 402.

From these various memory units, processing unit(s) 412 retrieves instructions to execute and data to process in order to execute the processes of the subject disclosure. The processing unit(s) can be a single processor or a multi-core processor in different implementations.

ROM 410 stores static data and instructions that are needed by processing unit(s) 412 and other modules of the electronic system. Permanent storage device 402, on the other hand, is a read-and-write memory device. This device is a non-volatile memory unit that stores instructions and data even when electronic system 400 is off. Some implementations of the subject disclosure use a mass-storage device (such as a magnetic or optical disk and its corresponding disk drive) as permanent storage device 402.

Other implementations use a removable storage device (such as a floppy disk, flash drive, and its corresponding disk drive) as permanent storage device 402. Like permanent storage device 402, system memory 404 is a read-and-write memory device. However, unlike storage device 402, system memory 404 is a volatile read-and-write memory, such a random access memory. System memory 404 stores some of the instructions and data that the processor needs at runtime. In some implementations, the processes of the subject disclosure are stored in system memory 404, permanent storage device 402, and/or ROM 410. From these various memory units, processing unit(s) 412 retrieves instructions to execute and data to process in order to execute the processes of some implementations.

Bus 408 also connects to input and output device interfaces 414 and 406. Input device interface 414 enables the user to communicate information and select commands to the electronic system. Input devices used with input device interface 414 include, e.g., alphanumeric keyboards and pointing devices (also called "cursor control devices"). Output device interfaces 406 enables, e.g., the display of images generated by the electronic system 400. Output devices used with output device interface 406 include, e.g., printers and display devices, such as cathode ray tubes (CRT) or liquid crystal displays (LCD). Some implementations include devices such as a touchscreen that functions as both input and output devices.

Also, as shown in FIG. 4, bus 408 also couples electronic system 400 to a network (not shown) through network interfaces 416. Network interfaces 416 may include, e.g., a wireless access point (e.g., Bluetooth or WiFi) or radio circuitry for connecting to a wireless access point. Network interfaces 416 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 400 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A method, comprising:
configuring one or more medical devices to connect to a predetermined temporary provisioning network of a healthcare organization responsive to the one or more medical devices being powered on for a first time by the healthcare organization, the temporary provisioning network being different than a healthcare network of the healthcare organization, wherein the healthcare network includes one or more services not accessible by the temporary provisioning network, and wherein the temporary provisioning network is publicly accessible, while the healthcare network is protected from unauthorized access;
receiving, at a first server remote from the healthcare organization, from the temporary provisioning network, one or more device identifiers corresponding to the one or more medical devices and an indication that the one or more medical devices requests access to the healthcare network;
receiving one or more security certificates for assignment to the one or more device identifiers;
determining, based on receiving the one or more certificates and the one or more device identifiers, that the received one or more device identifiers correspond to respective medical devices predetermined to receive access to a management server within the healthcare network; and
in accordance with a determination that the one or more medical devices are predetermined to receive access to the management server:
transmitting, through the temporary provisioning network to the one or more medical devices, a security certificate for configuring the one or more medical devices to access and communicate with the management server;
configuring, through the temporary provisioning network, the one or more medical devices with information to access the healthcare network and to communicate with the management server on the healthcare network using a new network connection based on the configuration information;
terminating communication between the one or more medical devices and the temporary provisioning network; and
transmitting, from the first server remote from the healthcare organization, an electronic signal informing the management server that the one or more medical devices have been configured to access and communicate with the management server.

2. The method of claim 1, wherein configuring the one or more medical devices to connect to a predetermined temporary provisioning network is performed by a production server distinct from the management server and coupled with the healthcare organization via a network external to the healthcare organization.

3. The method of claim 1, wherein the temporary provisioning network is configured to broadcast a service set identifier (SSID) preconfigured to be known by the medical devices and the medical devices are configured to seek the SSID prior to being powered on for a first time.

4. The method of claim 1, wherein the management server is configured to receive, via a user interface provided by the management server, an assignment of the one or more device identifiers to the one or more security certificates, the management server being further configured to provide to a provisioning server outside the healthcare organization the one or more security certificates to the one or more medical devices on a power up of the medical devices, and to communicate with the one or more medical devices after being informed that the one or more medical devices have been configured to access and communicate with the management server.

5. The method of claim 4, wherein the management server is configured to receive, via the user interface provided by the management server, an assignment of the one or more device identifiers and the one or more security certificates to a respective facility of a plurality of facilities within the healthcare organization, and wherein configuring the one or more medical devices to access and communicate with the management server comprises configuring the one or more medical devices to communicate via a local network within the respective facility, wherein the one or more security certificates are specific to the respective facility.

6. The method of claim 1, wherein the one or more device identifiers are network addresses of the respective medical devices.

7. The method of claim 1, wherein the indication that the one or more medical devices requests access to the healthcare network is received by the management server upon medical device power up.

8. The method of claim 1, wherein the one or more medical devices includes an infusion device, a ventilator device, a medicant dispensing device, a medication preparation device, or an automated dispensing device or a device coupled with an infusion device, a ventilator device, a medicant dispensing device, a medication preparation device, or an automated dispensing device.

9. The method of claim 1, wherein the configuring the medical devices to access and communication with the management server further comprises:
   verifying that the one or more security certificates have been installed successfully on the one or more medical devices; and
   transmitting, to the first server remote from the healthcare organization, a message indicating that security standards of the healthcare network have been met.

10. The method of claim 1, wherein configuring the medical devices further comprises:
   receiving an indication that the one or more medical devices have been successfully configured to access and communicate with the management server; and
   terminating a network access of the one or more medical devices to the predetermined temporary provisioning network.

11. A non-transitory machine-readable storage medium embodying instructions that, when executed by a machine, allow the machine to perform a method for automatic network provisioning, the method comprising:
   configuring one or more medical devices to connect to a predetermined temporary provisioning network of a healthcare organization responsive to the one or more medical devices being powered on for a first time, the temporary provisioning network being different than the healthcare network of the healthcare organization, wherein the healthcare network includes one or more services not accessible by the temporary provisioning network, and wherein the temporary provisioning network is publicly accessible, while the healthcare network is protected from unauthorized access;
   receiving, from the temporary provisioning network, one or more device identifiers corresponding to the one or more medical devices and an indication that the one or more medical devices requests access to the healthcare network;
   receiving one or more security certificates for assignment to the one or more device identifiers;
   determining, based on receiving the one or more certificates and the one or more device identifiers, that the received one or more device identifiers correspond to respective medical devices predetermined to receive access to a management server within the healthcare network;
   in accordance with a determination that the one or more medical devices are predetermined to receive access to the healthcare network and the management server;
   transmitting, through the temporary provisioning network to the one or more medical devices, a security certificate for configuring the one or more medical devices to access and communicate with the management server;
   configuring, through the temporary provisioning network, the medical devices with information to access the healthcare network and to communicate with the management server on the healthcare network using a new network connection based on the configuration information;
   terminating communication between the one or more medical devices and the temporary provisioning network; and
   providing a confirmation to the management server that the one or more medical devices have been configured to access and communicate with the management server.

12. The non-transitory machine-readable storage medium of claim 11, wherein configuring the one or more medical devices to connect to a predetermined temporary provisioning network is performed by a production server distinct from the management server and outside of the healthcare organization.

13. The non-transitory machine-readable storage medium of claim 11, wherein the temporary provisioning network is configured to broadcast a service set identifier (SSID) pre-configured to be known by the medical devices and the medical devices are configured to seek the SSID prior to being powered on for a first time.

14. The non-transitory machine-readable storage medium of claim 11, wherein the management server is configured to receive, via a user interface provided by the management server, an assignment of the one or more device identifiers to the one or more security certificates, the management server being further confirmed to provide to a provisioning server outside the healthcare organization the one or more security certificates to the one or more medical devices on a power up of the medical devices, and to communicate with the one or more medical devices after being informed that the one or more medical devices have been configured to access and communicate with the management server.

15. The non-transitory machine-readable storage medium of claim 14, wherein the management server is configured to receive, via the user interface provided by the management server, an assignment of the one or more device identifiers and the one or more security certificates to a respective facility of a plurality of facilities within the healthcare organization, and wherein configuring the one or more medical devices to access and communicate with the management server comprises configuring the one or more medical devices to communicate via a local network within the respective facility, wherein the one or more security certificates are specific to the respective facility.

16. The non-transitory machine-readable storage medium of claim 11, wherein the configuring the medical devices to access and communication with the management server further comprises:
   verifying that the one or more security certificates have been installed successfully on the one or more medical devices; and
   determining security standards of the healthcare network have been met.

17. The non-transitory machine-readable storage medium of claim 11, wherein the one or more device identifiers are network addresses of the respective medical devices.

18. The non-transitory machine-readable storage medium of claim 11, wherein the indication that the one or more medical devices requests access to the healthcare network is received by the management server upon medical device power up.

19. The non-transitory machine-readable storage medium of claim 11, wherein configuring the medical devices further comprises:
   receiving an indication that the one or more medical devices have been successfully configured to access and communicate with the management server; and
   terminating the predetermined temporary provisioning network.

20. A system, comprising:
   one or more processors; and
   memory including instructions that, when executed by the one or more processors, cause the one or more processors to:
   configure one or more medical devices to connect to a predetermined temporary provisioning network of a healthcare organization responsive to the one or more medical devices being powered on for a first time, the temporary provisioning network being different than the healthcare network of the healthcare organization, wherein the healthcare network includes one or more services not accessible by the temporary provisioning network, and wherein the temporary provisioning network is publicly accessible, while the healthcare network is protected from unauthorized access;
   receive, from the temporary provisioning network, one or more device identifiers corresponding to the one or more medical devices and an indication that the one or more medical devices requests access to the healthcare network;
   receive one or more security certificates for assignment to the one or more device identifiers;
   determine, based on receiving the one or more certificates and the one or more device identifiers, that the received one or more device identifiers correspond to respective medical devices predetermined to receive access to a management server within the healthcare network;
   in accordance with a determination that the one or more medical devices are predetermined to receive access to the healthcare network and the management server;
   transmit, through the temporary provisioning network to the one or more medical devices, a security certificate for configuring the one or more medical devices to access and communicate with the management server;
   configure, through the temporary provisioning network, the medical devices with information to access the healthcare network and to communicate with the management server on the healthcare network using a new network connection based on the configuration information;
   terminate communication between the one or more medical devices and the temporary provisioning network; and
   provide a confirmation to the management server that the one or more medical devices have been configured to access and communicate with the management server.

21. A medical device, comprising:
   a non-volatile data storage unit storing (a) predetermined provisioning network connection information and (b) identification information uniquely identifying the medical device;
   one or more processors; and
   memory including instructions that, when executed by the one or more processors, cause the one or more processors to:
   upon activation of the medical device, determine that the activation is an initial activation at a healthcare facility based at least in part on an activation indicator stored by the medical device;
   establish, responsive to determining the activation is the initial activation, a first network connection with a provisioning server via a provisioning network based at least in part on the predetermined provisioning network connection information;
   transmit, to the provisioning server via the first network connection, the identification information uniquely identifying the medical device;
   receive, from the provisioning server, a security certificate for configuring the medical device to access and communicate with the management server, the security certificate being associated with an identifier for the medical device;
   receive, from the provisioning server via the first network connection, facility network connection information for accessing and communicating with a management server associated with the healthcare facility via a healthcare network different than the provisioning network, wherein the healthcare network includes one or more services not accessible by the provisioning network, and wherein the provisioning network is publicly accessible, while the healthcare network is protected from unauthorized access;
   terminate communication with the provisioning network; and
   establish, after receiving the facility network connection information and terminating communication with the provisioning network, using the healthcare network different than the provisioning network, a second network connection with the management server based at least in part on the facility network connection information.

22. The medical device of claim 21, wherein the provisioning network connection information comprises a service set identifier (SSID), and wherein establishing the first network connection comprises wirelessly scanning for a broadcast message including the SSID.

23. The medical device of claim 21, wherein the memory includes instructions to further cause the one or more processors to, upon establishing the second network connection, close the first network connection.

* * * * *